(12) United States Patent
Murray (10) Patent No.: US 8,220,454 B2
(45) Date of Patent: Jul. 17, 2012

(54) LARYNGEAL MASK DEVICE

(75) Inventor: James Murray, Belfast (GB)

(73) Assignee: James Murray, Belfast (GB)

( * ) Notice: Subject to any disclaimer, the term of this patent is extended or adjusted under 35 U.S.C. 154(b) by 932 days.

(21) Appl. No.: 12/158,505

(22) PCT Filed: Dec. 20, 2006

(86) PCT No.: PCT/EP2006/012333
§ 371 (c)(1),
(2), (4) Date: Jun. 20, 2008

(87) PCT Pub. No.: WO2007/071407
PCT Pub. Date: Jun. 28, 2007

(65) Prior Publication Data
US 2009/0000622 A1    Jan. 1, 2009

(30) Foreign Application Priority Data
Dec. 23, 2005  (GB) .................................. 0526350.4

(51) Int. Cl.
*A61M 16/00*   (2006.01)
(52) U.S. Cl. .......... 128/200.26; 128/207.15; 128/207.16
(58) Field of Classification Search ............ 128/200.26, 128/207.15–207.16
See application file for complete search history.

(56) References Cited

U.S. PATENT DOCUMENTS

| | | | | |
|---|---|---|---|---|
| 5,791,341 A * | 8/1998 | Bullard | | 128/207.15 |
| 5,896,858 A * | 4/1999 | Brain | | 128/207.15 |
| RE39,938 E * | 12/2007 | Brain | | 128/207.15 |
| 2004/0020491 A1 | 2/2004 | Fortuna | | |
| 2004/0079364 A1 * | 4/2004 | Christopher | | 128/200.26 |
| 2006/0124132 A1 * | 6/2006 | Brain | | 128/207.14 |
| 2006/0180155 A1 * | 8/2006 | Glassenberg et al. | | 128/207.15 |

FOREIGN PATENT DOCUMENTS

WO    WO 02/092144 A2    11/2002
WO    WO 03/020340 A2    3/2003

OTHER PUBLICATIONS

International Search Report dated Mar. 27, 2007 (three (3) pages).

* cited by examiner

*Primary Examiner* — Lynne Anderson
(74) *Attorney, Agent, or Firm* — Sullivan & Worcester LLC; Christopher T. McWhinney (57) ABSTRACT

An airway device (10) comprising an airway tube (14) and a laryngeal mask (12). The mask has an inflatable cuff (36) which has a tip (38) for insertion, in use, into a patient's oesophagus. The mask further includes a guide member (42) projecting from the tip of the cuff. The guide member carries an inflatable balloon (60) for blocking the patient's oesophagus during use. The guide member helps to position the mask correctly and reduces the risk of pulmonary aspiration of gastric contents during use.

22 Claims, 9 Drawing Sheets

LARYNGEAL MASK DEVICE

FIELD OF THE INVENTION

The present invention relates to devices for maintaining the integrity of the airway, and in particular to laryngeal mask devices.

BACKGROUND OF THE INVENTION

Laryngeal mask devices are well known and are commonly referred to as laryngeal mask airways (LMAs). LMAs are used to facilitate breathing, for example when a patient is anaesthetized or unconscious, and to allow insertion of endotracheal tubes, or other medial instruments into the laryngeal opening and/or trachea of the patient. LMAs normally include a laryngeal mask connected to an airway tube, the mask being located, in use, over the laryngeal opening to provide a direct passage, or airway, from the laryngeal opening to the external environment via the airway tube. The tip of the mask, when in use, is located in the upper oesophageal opening in order to provide accurate placement as an airway device and also to reduce the risk of pulmonary aspiration of gastric contents.

A problem with conventional LMAs is that they can be difficult to install properly, with the result that the device may function inadequately as an airway, and that the patient is not reliably protected against pulmonary aspiration.

SUMMARY OF THE INVENTION

Accordingly, a first aspect of the invention provides an airway device comprising an airway tube and a mask, the mask comprising an aperture or lumen in fluid communication with the airway tube and surrounded by a peripheral cuff having a tip for insertion, in use, into a patient's oesophagus, wherein the mask further includes a guide member projecting beyond the tip. Preferably, the cuff, or at least part of it, is inflatable.

The guide member preferably extends from the tip itself and, advantageously, is generally, or substantially, coplanar or collinear with the airway tube. In preferred embodiments, the guide member is curved. The airway tube is typically also curved, in which case the guide member and airway tube are advantageously substantially coplanar. More preferably the plane in which the guide member and airway tube lie is substantially perpendicular with the obverse face of the mask.

In preferred embodiments, the guide member carries, or includes, a blocking member in the preferred form of an inflatable balloon. The balloon is arranged to block the patient's oesophagus when inflated.

It is further preferred that the mask includes a ramp extending from the lumen. The ramp serves, in use, as a guide for objects, such as medical instruments, that are fed through the airway tube to emerge from the lumen. One end of the ramp is located at or adjacent the lumen, the other end being free or unobstructed. In preferred embodiments, the ramp is aligned with the airway tube such that an object emerging from the airway tube via the lumen engages with the ramp and may be directed therealong, the free end of the ramp directing the object clear of the mask.

A second aspect of the invention provides an airway device comprising an airway tube and a mask, the mask comprising an aperture or lumen in fluid communication with the airway tube and surrounded by a peripheral cuff having a tip for insertion, in use, into a patient's oesophagus, wherein a blocking member, in the preferred form of an inflatable balloon, is provided at or adjacent said tip.

A third aspect of the invention provides an airway device comprising an airway tube and a mask, the mask comprising an aperture or lumen in fluid communication with the airway tube and surrounded by a peripheral cuff, wherein the mask includes a ramp extending from the lumen.

Further advantageous aspects and preferred features of the invention will become apparent to those ordinarily skilled in the art upon review of the following description of a preferred embodiment and with reference to the accompanying drawings.

BRIEF DESCRIPTION OF THE DRAWINGS

Embodiments of the invention are now described by way of example and with reference to the accompanying drawings in which like numerals are used to indicate like parts and in which.

DETAILED DESCRIPTION OF THE DRAWINGS

Referring now in particular to FIGS. 1 to 5 of the drawings, there is shown, generally indicated as 10, an airway device, or laryngeal mask device embodying the invention. The device 10 includes a laryngeal mask 12 connected or coupled to an airway tube 14.

The mask 12 comprises a body portion 16 having an obverse face 18 and a reverse face 20. An aperture or lumen 22 is defined in the obverse face 18. In use, the lumen 22 is in fluid communication with the interior of the airway tube 14. To this end, the body 16 may include a stem or socket 24 one end of which opens onto the lumen 22, the other end being adapted to receive an end of the airway tube 14. The tube 14 may be detachably mountable on the socket 24. Alternatively, the tube 14 and the body 16 (or socket 24) may be integrally formed. As shown in the drawings, the socket 24 conveniently projects from the reverse face 20 of the body 16.

The mask 12 further includes a cuff 26 which extends around the periphery of the body 16 such that it also extends around the periphery of the lumen 22. Hence, the mask 12 may be said to comprise an obverse face, which includes the lumen 22, the obverse face 18 of the body 16 and one face of the cuff 26, and a reverse face, which includes the reverse face 20 of the body 16, the opposite face of the cuff 26 and an interface between the tube 14 and the body 16.

In preferred embodiments, the cuff 26 is inflatable and may be formed any suitable material, for example, from any suitable plastics, silicone or rubber. To inflate the cuff 26, an inflation device is provided, conveniently in the form of a balloon pump 32 with a valve 34. The pump 32 is typically connected to the cuff 26 by an inflation tube 36 such that the pump is in fluid communication with the interior of the cuff 26. Conveniently, the valve 34 is configurable to allow fluid (normally air) to be introduced into the cuff 26 (by the action of the pump 32) when it is desired to inflate the cuff 26, and to allow fluid to escape from the cuff 26 when it is desired to deflate the cuff 26. Preferably, the cuff 26 is formed from neoprene rubber, or similar material, in order that it may, after deflation, consistently conform to the desired shape. Alternatively, the cuff 26 may be formed from silicone.

The mask 12 has a tip portion 38 which, in use, is seated in the mouth or opening of a patient's oesophagus (not shown), the remainder of the mask 12 being located over the laryngeal opening with the lumen 22 positioned over, and facing, the trachea. Normally, the tip 38 is provided by part of the cuff 26.

The portion of the airway tube 14 that interfaces with the body 16 (and/or the socket 24) is advantageously obliquely disposed with respect to the body 16 such that said portion of the tube 14 (and/or the socket 24) extends away from the reverse face 20 in a direction that is substantially opposite the direction in which the tip 38 lies with respect to the interface.

Figure 5:
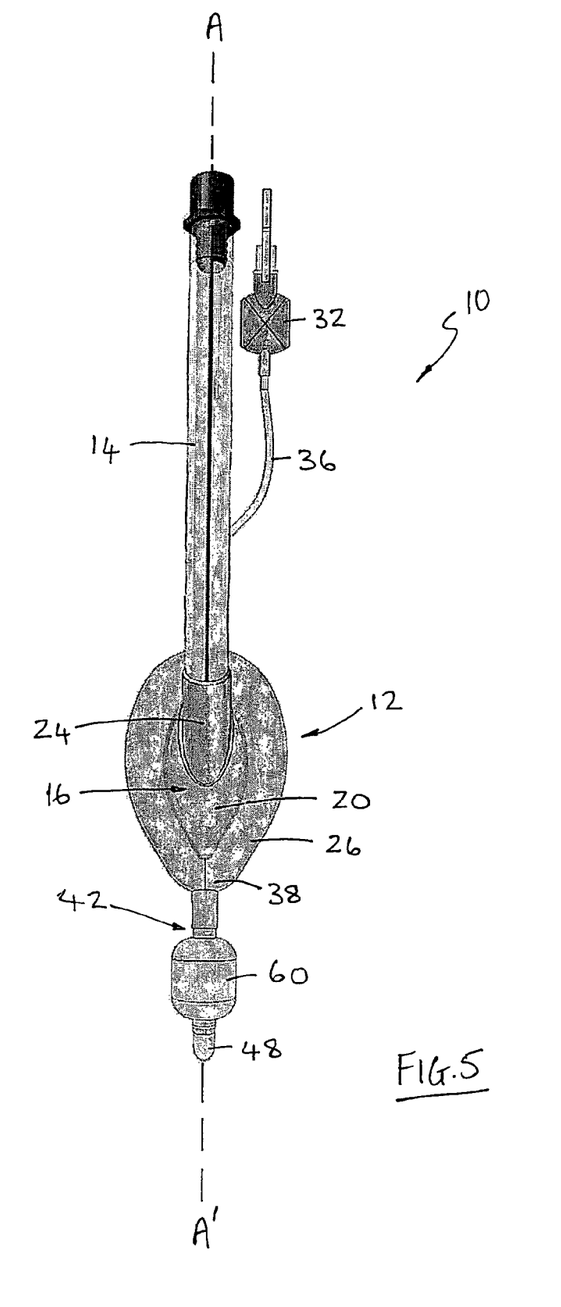
FIG. 5 is a plan view of the device of FIG. 1.
Figures 6, 7, 8:
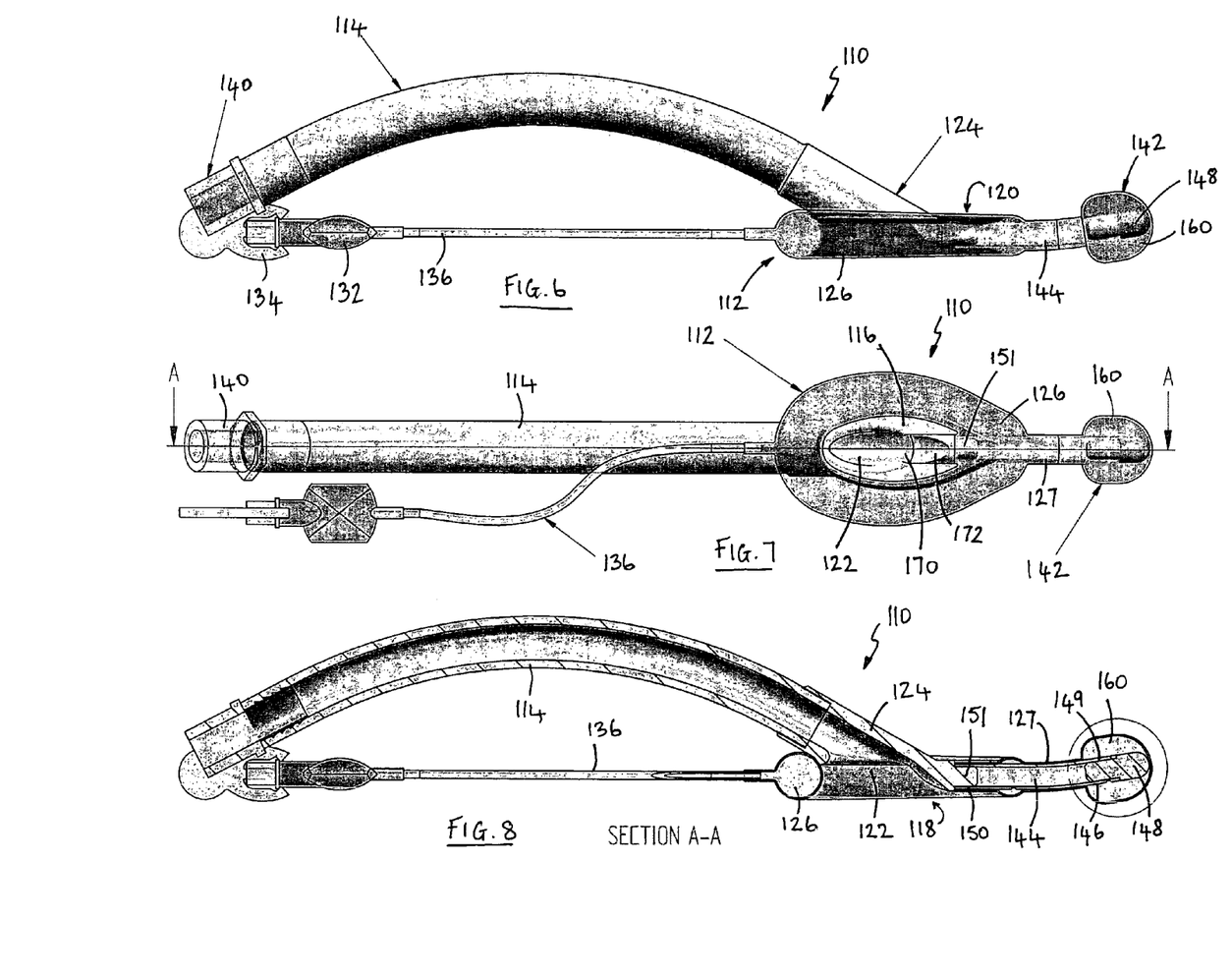
FIG. 6 is a side view of an alternative airway device embodying the invention.
FIG. 7 is a plan view of the device of FIG. 6.
FIG. 8 is a sectioned side view of the device of FIGS. 6 and 7.
Figure 8A:
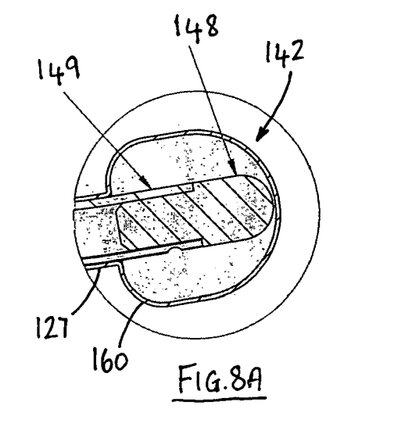
FIG. 8A is a detail of the sectioned view of FIG. 8.
Figure 9:
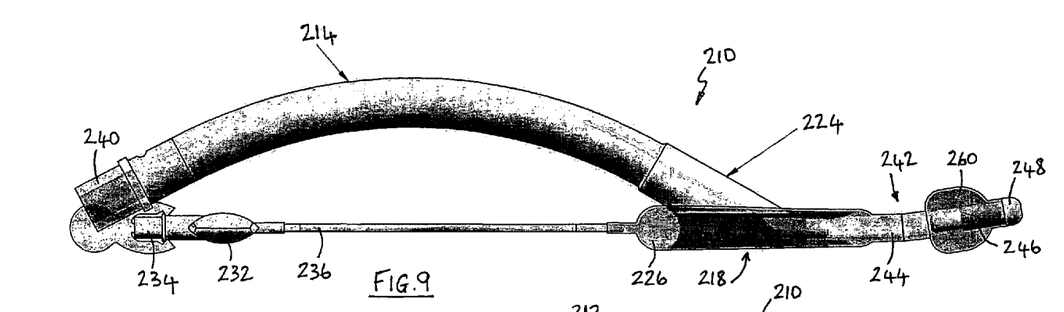
FIG. 9 is a side view of a further alternative airway device embodying the invention.
Figure 9A:
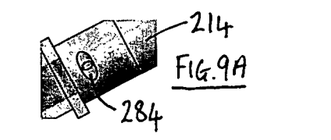
FIG. 9A is a plan view of a detail of the device of FIG. 9.
Figure 10:
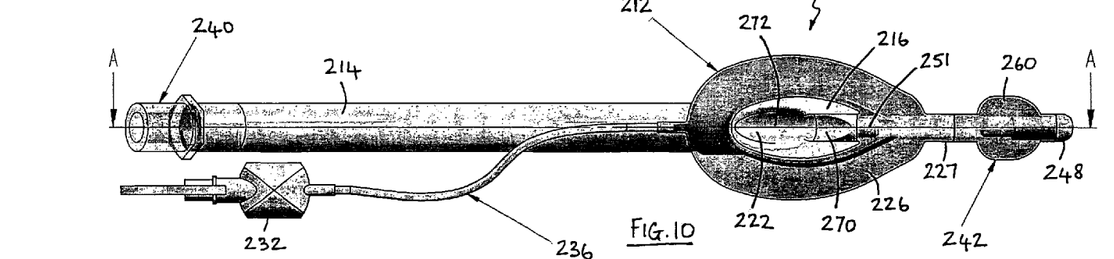
FIG. 10 is a plan view of the device of FIG. 9.
Figure 11:
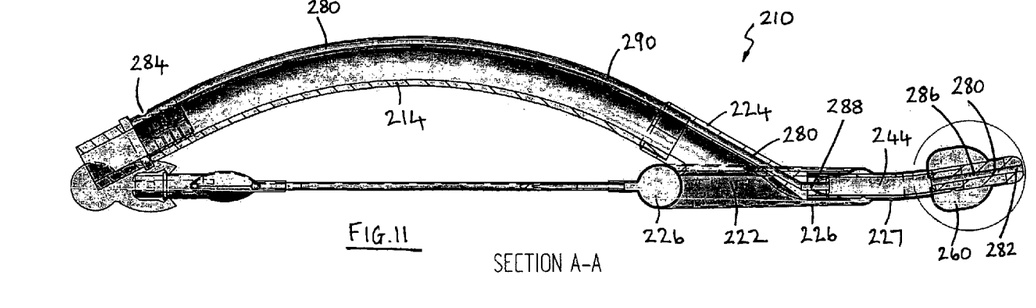
FIG. 11 is a sectioned side view of the device of FIGS. 9 and 10.
Figure 11A:
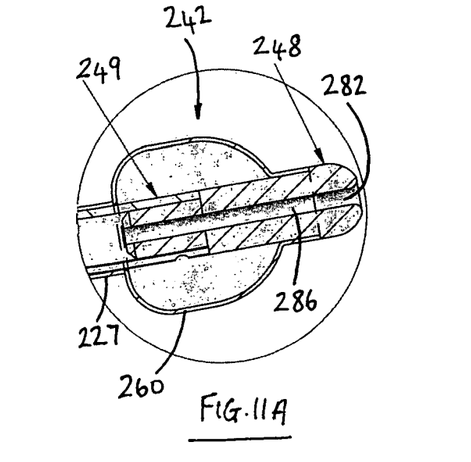
FIG. 11A is a detail of the sectioned view of FIG. 11.
Figure 12:
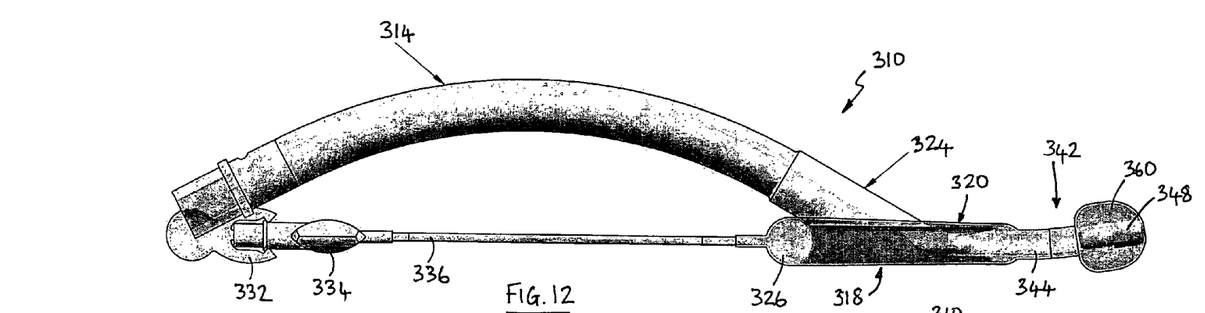
FIG. 12 is a side view of a further alternative airway device embodying the invention.
Figure 12A:
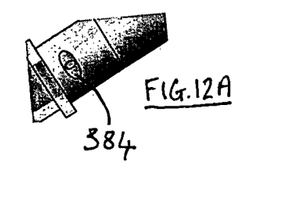
FIG. 12A is a plan view of a detail of the device of FIG. 12.
Figure 13:
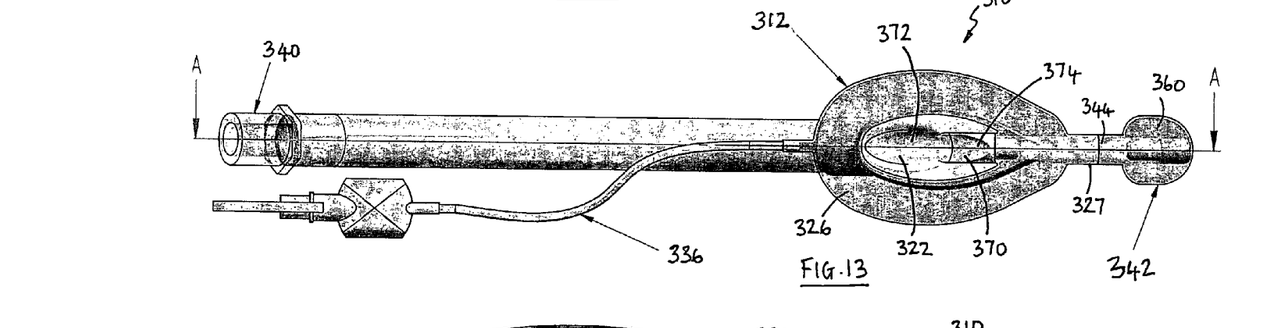
FIG. 13 is a plan view of the device of FIG. 12.
Figure 14:
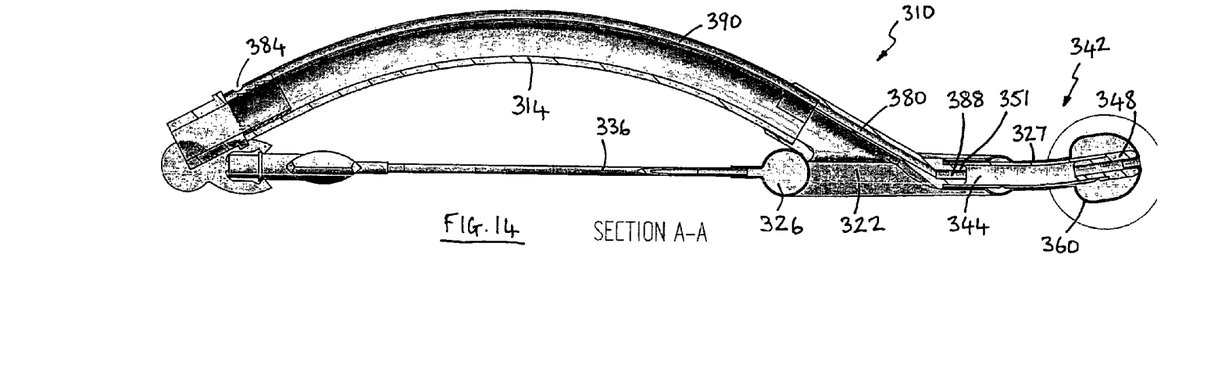
FIG. 14 is a sectioned side view of the device of FIGS. 12 and 13.
Figure 14A:
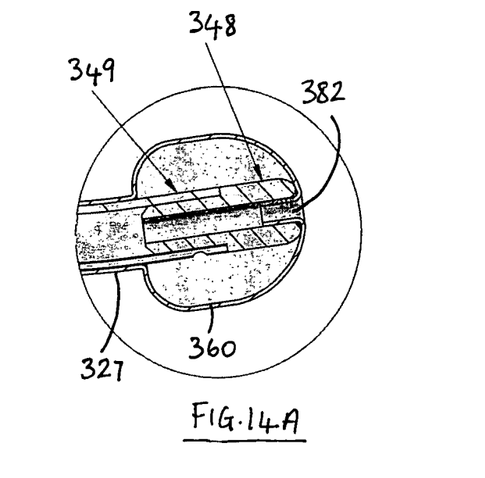
FIG. 14A is a detail of the sectioned view of FIG. 14.

In FIG. 5, a notional axis A-A' is shown, the axis running through the tip 38 and the interface between the tube 14 and the body 16. The tube 14 itself conveniently extends from the mask 12 substantially along the axis A-A' such that the axis A-A' may be considered to be the longitudinal axis of the device 10.

The tube 14 is preferably curved to form an arc, or arc-like shape, having its concave side facing said axis A-A' (or facing the plane in which the obverse face of the mask 12 lies). By way of example, the radius of curvature of the tube 14 (measured to the centre of the tube) is approximately 153 mm. The straightened length of the tube 14 may be approximately 180 mm. The tube 14 may have an inner diameter of approximately 11 mm and an outer diameter of approximately 16 mm. The tube 14 is preferably formed from a flexible material such as plastics, e.g. PVC. In preferred embodiments, the acute angle made between the tube 14 and the body 16 at the interface is between approximately 20° and 60° inclusive. The preferred curvature of radius is between approximately 20° and 160° inclusive.

The distal end of the tube 14, i.e. the end remote from the mask 12, may carry a connector 40 for connection to, for example, a respiratory apparatus (not shown) or for receiving other medical instruments (not shown). In particular, it is preferred that the connector 40 and the tube 14 are dimensioned to receive a conventional tracheal tube (not shown). The tube 14 may be provided with markings (not shown) for indicating the depth to which the device 10 is inserted into a patient during use. A bite block (not shown) may be provided on the tube 14 on which a patient may bite during use.

In accordance with one aspect of the invention, a guide member or projection 42 is provided on the mask 12. The guide 42 advantageously emanates from the tip 38 of the mask 12 (or at least from adjacent the tip 38) but, in any event, projects beyond the tip 38 with respect to the mask 12. Preferably, the guide 42 projects from the mask 12 in a direction substantially along, or substantially parallel with, the axis A-A' when viewed in plan (e.g. see FIG. 5). The guide 42 is preferably substantially co-linear with the tube 14 when viewed in plan but, more generally, may be substantially co-planar with the tube 14. Advantageously, the guide 42, or at least its free end, is obliquely disposed with respect to the body 16, or, more particularly, the plane in which the obverse or reverse face of the body lies. In the embodiment of FIGS. 1 to 5, the guide 42 is inclined downwardly (as viewed), i.e. in substantially the same direction in which the obverse face 18 faces. In alternative embodiments (see FIGS. 6 to 14) the guide is inclined upwardly (as viewed), i.e. in substantially the same direction in which the reverse face 20 faces.

In preferred embodiments, the guide 42 is curved to form an arc, or arc-like, shape. The guide 42 may be curved in the same sense as the tube 14, as is for example illustrated in FIGS. 1 to 5. Hence, taking the plane in which the obverse face of the mask 12 lies as a reference, the concave side of the guide 42 faces away from said plane. In other embodiments, however, the guide is curved in substantially the opposite sense to the tube, as is illustrated in FIGS. 6 to 14 described hereinafter. Preferably, the guide 42 and tube 14 are substantially coplanar, lying in a plane that is substantially perpendicular with the plane in which the obverse face of the mask 12 lies. The radius of curvature of the guide 42 (measured to the centre of the guide) may, for example, be approximately 150 mm. The straightened length of the guide 42 (or the part of the guide 42 that projects beyond the mask 42) may be, for example, approximately 10-140 mm.

In the preferred embodiment, the guide 42 includes a substantially straight support portion or stem 44 that projects from the mask 12 substantially along said axis A-A', and a curved portion 46 which may, for example, be curved in the manner described above. The free end 48 of the guide 42 may be tapered (as shown) but is preferably rounded.

The guide 42, particularly the portions 44, 46, may take any suitable form, for example a solid member or a hollow tube. It is preferred that the guide 42 is flexible and, preferably still, resilient, and may for example, be formed from plastics.

The guide 42 may be fixed to, or detachably mounted on, the mask 12 in any convenient manner. In the illustrated embodiment, one end 50 of the guide 42 is connected to the body 16 of the mask 12. To this end, the body 16 of the mask 12 includes a connector 51 (for example a male connector) and the end 50 of the guide 42 includes a co-operating connector (for example a female connector). When connected to the body 16, the guide 42 passes through the cuff 26. This may be achieved by providing a sleeve-like portion 27 in the cuff 26, or by sealing the cuff 26 around the guide 42.

Figure 1:
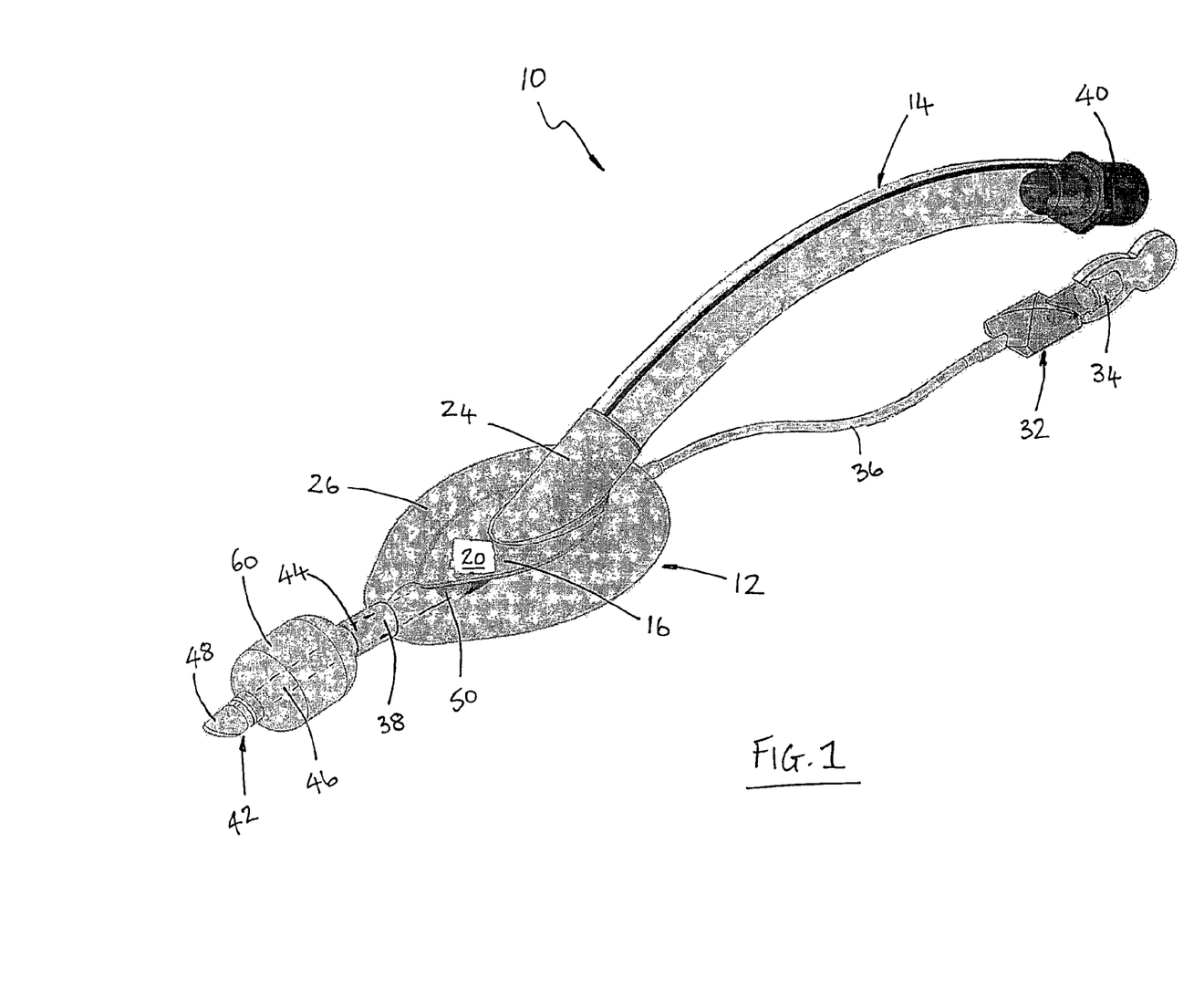
FIG. 1 is a perspective view of an airway device embodying the invention.
Figure 2:
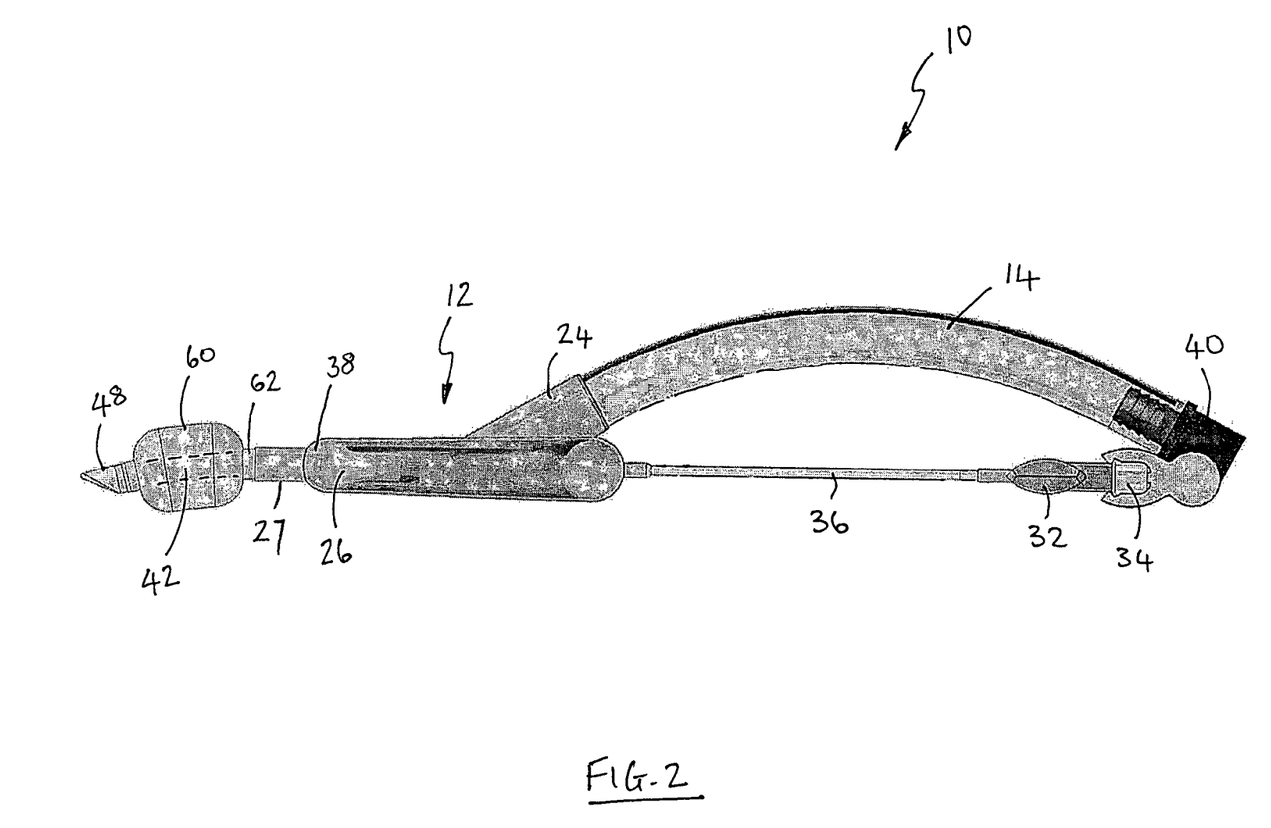
FIG. 2 is a side view of the device of FIG. 1.
Figure 3:
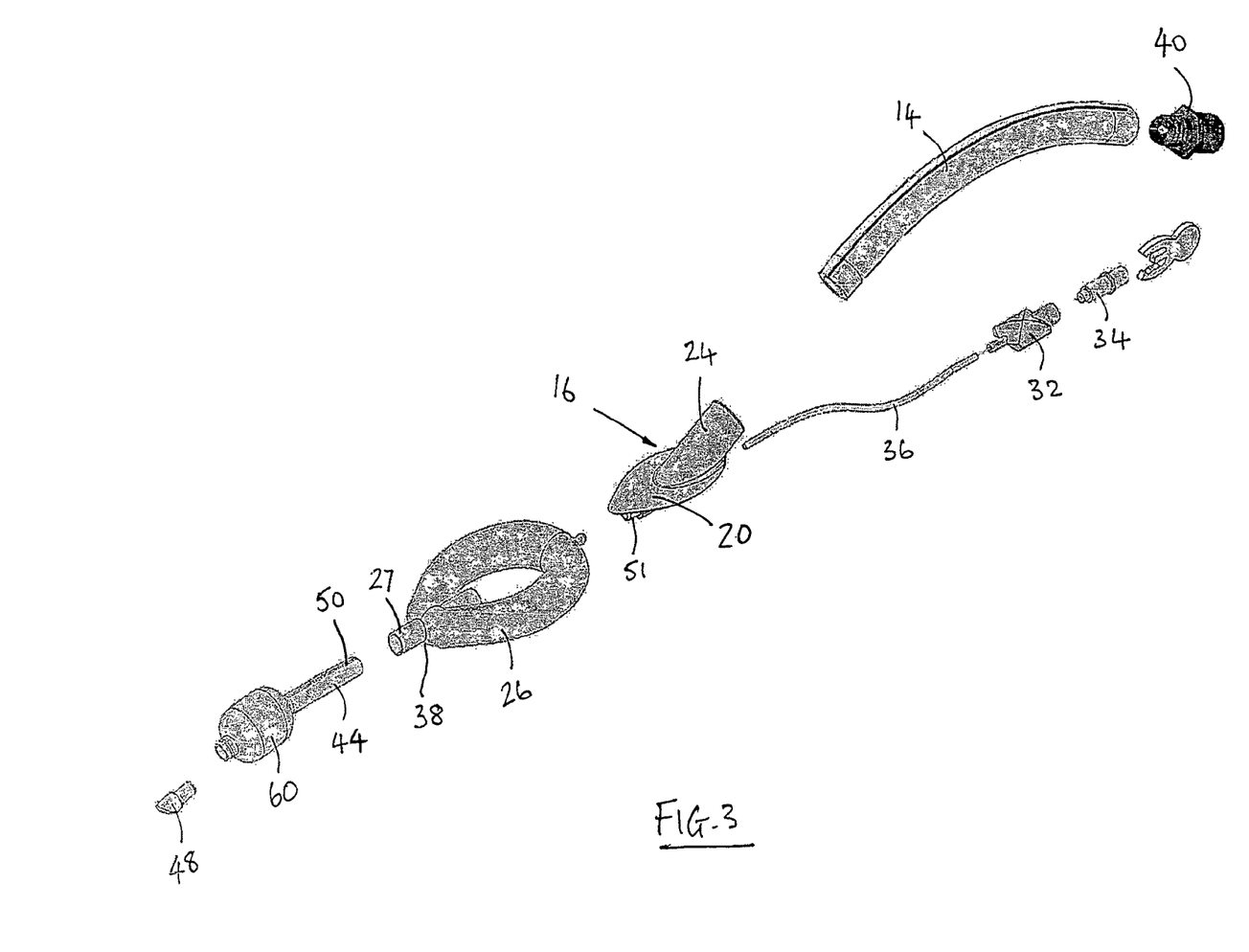
FIG. 3 is an exploded perspective view of the device of FIG. 1.

In accordance with a second aspect of the invention, the guide 42 carries a blocking member, preferably in the form of an inflatable sack or balloon 60, although the blocking member may alternatively be non-inflatable. The balloon 60 may be located at the end of the guide 42 or, as in the illustrated embodiment, may be located intermediate the mask 12 and the free end 48 of the guide 42. The guide 42 may pass through the balloon 60 and, to this end, the balloon 60 may include a sleeve-like aperture for receiving the guide 42, or may be sealed around the guide 42. Alternatively still, the end 48 of the guide 42 may be detachably mountable on the balloon 60 (as shown in FIG. 3) in which case it is not necessary for a portion of the guide to pass through the balloon 60 (the balloon may be considered to be part of the guide) and, optionally, the portion of the guide 42 that extends between the cuff 26 and the balloon 60 may comprise a tube for allowing fluid communication between the interior of the cuff 26 and the interior of the balloon 60.

The balloon 60 includes at least one inlet/outlet (not visible) by which the balloon 60 may be inflated and deflated. In preferred embodiments, the interior of the balloon 60 is in fluid communication with the interior of the cuff 26 such that the balloon is inflated when the cuff 26 is inflated, and deflated when the cuff 26 is deflated. In alternative embodiments, the balloon 60 may be inflated/deflated by a separate inflation apparatus (not shown) which may, for example, be similar to the balloon pump assembly described above and illustrated in the drawings.

In the illustrated embodiment, the balloon 60 has an inlet/outlet in the form of a double walled tubular neck 62, the inner wall being seated around the guide member portion 44, the gap between the walls opening into the interior of the cuff 26 to provide fluid communication between the cuff 26 and the balloon 60. In alternative embodiments, fluid communication between the cuff 26 and the balloon 60 may be provided in any convenient manner, e.g. by a tube (not shown) extending between the cuff 26 and the balloon 60. Alternatively, the neck of the balloon may be single-walled and may engage directly upon the guide member portion 44, air, or other gas, forcing its way between the neck portion and the guide member portion 44 during the inflation/deflation processes. Similarly, the cuff 26 has a neck portion 27 which may be double-walled, but which is conveniently single walled and engages with the guide member portion 44. The balloon 60, especially when deflatable, is preferably formed from neoprene rubber, or similar material, but may alternatively be formed from other material, e.g. silicone or PVC.

In use, with the balloon 60 and cuff 26 deflated, the device 10 is inserted, mask first, through the patient's mouth. The guide 42 is fed into the patient's oesophagus. As a result, the tip 38 of the mask 12 is lead into the mouth of the oesophagus whereupon it can be fed no further. The tip 38 is thus correctly seated in the mouth of the oesophagus. Consequently, the mask 12 itself is correctly positioned in the oropharynx over the laryngeal mouth. The cuff 26 and the balloon 60 may then be inflated. The inflated cuff 26 helps to secure the mask in its correct position. The inflated balloon 60 helps not only to secure the device 10 in the correct position, but also blocks the oesophagus thereby preventing aspiration of the gastric contents. In order to remove the device 10, the cuff 26 and, where possible, the balloon 60 are first deflated.

Figure 4:
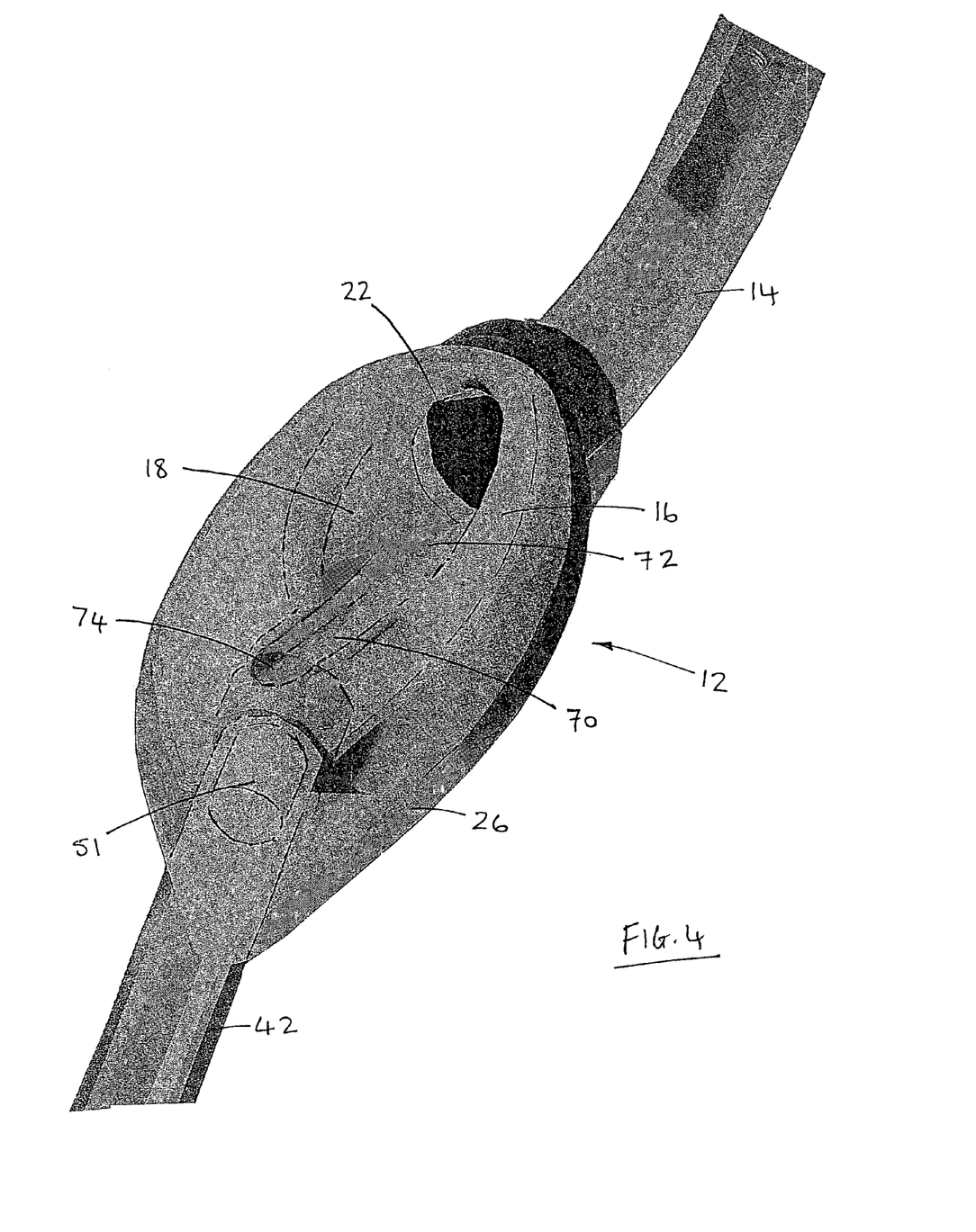
FIG. 4 is a perspective view of part of the device of FIG. 1.

Referring now in particular to FIG. 4, the preferred mask 12 includes a ramp 70 extending from the lumen 22. In the illustrated embodiment, the body 16 is shaped to define the ramp 70 in its obverse face 18. The ramp 70 has a first end 72 located at or adjacent the lumen 22 and a second unobstructed end 74 located at or adjacent the obverse face of the mask 12. The ramp 70 is aligned with the lumen 22 such that the leading end of an object (not shown), such as a medial instrument, that is fed through the airway tube 14 to the mask 12, engages with the ramp 70 as it emerges from the lumen 22 and thereafter is directed by the ramp 70 as it continues to be fed through the tube 14. The end 74 of the ramp is unobstructed such that the leading end of the object may pass freely beyond the mask 12. The ramp 70 is advantageously aligned with the tube 14 and/or the socket 24 in order that it may serve as a continuation of the inner walls/surface of the tube 14 and/or socket 24. The ramp 70 is preferably curved, the curvature being in a sense and to a degree that is the same or similar to the curvature of the tube 14 and/or the socket 24. In use, the ramp 70 facilitates the insertion of an instrument or other object into the patient's trachea once the mask 12 is correctly fitted. To this end, the surface of the ramp 70 is sufficiently smooth to allow such an instrument, especially a tracheal tube, to slide therealong.

In one mode of use, when the device 10 is inserted, a bougie (not shown) may be introduced into the patient's trachea via the tube 14. Then, the device 10 may be removed, leaving the bougie in place. The bougie may then be used as a guide for the insertion of another instrument, e.g. a tracheal tube (not shown). It will be seen therefore that it is not necessary that the tube 14 itself be wide enough to receive a tracheal tube.

FIGS. 6 to 14 of the drawings illustrate three further embodiments of the invention, each being generally similar to the embodiment described above with reference to FIGS. 1 to 5. Hence, as would be apparent to a skilled person, the description provided above in relation to FIGS. 1 to 5 applies also to the embodiments of FIGS. 6 to 14 and like numerals are used to indicate like parts. Key differences between embodiments are described below, although a skilled person may also note further differences by comparison of the drawings. Moreover, as would be apparent to a skilled person, the features of each embodiment may be used with any other embodiment.

Referring now to FIGS. 6 to 8A, there is shown an laryngeal mask device 110. The device 110 has a guide 142 which is inclined, and is preferably curved, in substantially the same direction in which the reverse face 120 of the body 116 faces. It is found that inclination and/or curvature in this direction is particularly advantageous in facilitating location of the guide 142 in the oesophagus during use. The guide 142 may comprise a support portion 144, 146 one end 150 of which is connectable to the body 116 at connector 151. The other end 149 is connectable, preferably detachably, to the tip portion 148 which may, for example be formed from a relatively soft material such as rubber. The free end of the tip 148 is preferably rounded. The support portion 144, 146 may take the form of a tube, or may at least have a socket formed at each end.

The blocking member, which preferably takes the form of an inflatable balloon 160, optionally encloses the tip 148, such that the tip 148 does not project through or beyond the balloon 160. The interior of the balloon 160 is preferably in fluid communication with the interior of the cuff 126 so that both may be inflated and deflated by the same action, e.g. by the action of the pump and valve unit 132, 134. To this end, the cuff 126 and the balloon 160 may be connected or conjoined by an outer skin 161 which passes over the support 144, 146.

Referring now to FIGS. 9 to 11A, there is shown an laryngeal mask device 210. The device 210 includes a venting channel 280 one end 282 of which opens to the external environment at the tip 248, the other end 284 opening to the external environment beyond the mask 212 with respect to the tip 248. Conveniently, said other end 284 (see FIG. 9A in particular in which said other end 284 is shown as a vent hole) is located at or adjacent the free end of the tube 214 which, in use, is located externally of the patient. The venting channel 280 provides a passageway through which gases may pass during use to relieve pressure which may otherwise build up in the patient's oesophagus. In the embodiment of FIGS. 9 to 11A, the tip 248 projects beyond the balloon 260 with respect to the mask 212, the balloon 260 being sealed around the tip 248 in any convenient manner to allow it to be inflated. The tip 248 includes a bore 286 running from the open end 282 into the support 244, 246, the support 244, 246 being hollow (or at least including a co-operable bore). The venting channel 280 continues in this example by means of a bore 288 formed in the connector 251. A venting passage or tube 290 runs along the main tube 214 (e.g. along its outside wall) to connect the vent hole 284 to, in this case, the bore 288. The venting passage or tube 290 may be co-formed with the main tube 214.

Referring now to FIGS. 12 to 14A, there is shown an laryngeal mask device 310 which is similar to the device 210 especially in the provision of a venting channel 380. In this embodiment, however, the tip 348 does not project beyond the balloon 360 (or other blocking member). In the illustrated embodiment, the balloon 360 is sealed around the mouth of the end 282 in any convenient manner to allow the balloon 260 to be inflated.

The invention is not limited to the embodiments described herein which may be modified or varied without departing from the scope of the invention.

The invention claimed is:

1. An airway device comprising:
   an airway tube;
   a laryngeal mask, the mask being shaped to define an aperture, the aperture being in fluid communication with the airway tube;
   a peripheral cuff at least partly surrounding said aperture, the cuff having a tip for insertion, in use, into a patient's oesophagus;
   a guide member projecting from said tip of said peripheral cuff and having a free end spaced apart from said tip; and
   a blocking member, provided on said guide member, for blocking, in use, said patient's oesophagus, wherein said blocking member comprises an inflatable balloon that encloses said free end of the guide member.

2. A device as claimed in claim 1, wherein the cuff, or at least part of it, is inflatable.

3. A device as claimed in claim 2, further including means for inflating said cuff.

4. A device as claimed in claim 1, in which said aperture is provided in an obverse face of said mask, said guide member being inclined, with respect to the mask, in a direction generally opposite the direction in which said obverse face faces.

5. A device as claimed in claim 1, in which said guide member, or at least a free end of said guide member is curved.

6. A device as claimed in claim 5, in which said aperture is provided in an obverse face of said mask, said guide member being inclined, with respect to the mask, in a direction generally opposite the direction in which said obverse face faces, and in which the guide member is curved in a direction generally opposite the direction in which said obverse face faces.

7. A device as claimed in claim 6, wherein said airway tube is curved and wherein the airway tube and guide member are curved in substantially opposite directions with respect to the mask.

8. A device as claimed in claim 1, wherein the respective longitudinal axes of said airway tube and said guide member are substantially co-linear.

9. A device as claimed in claim 1, wherein said airway tube is curved.

10. A device as claimed in claim 1, in which the guide member carries, or includes, a blocking member shaped and dimensioned to substantially block a patient's oesophagus during use.

11. A device as claimed in claim 1, wherein the cuff, or at least part of it, is inflatable and wherein the respective interiors of said cuff and said balloon are in fluid communication with one another.

12. A device as claimed in claim 1, wherein said mask comprises a body in which said aperture is formed, the body having an obverse face extending between said peripheral cuff and said aperture, the body further including a ramp extending from said aperture, said ramp being aligned with said airway tube and being raised with respect to said obverse face.

13. A device as claimed in claim 12, wherein a first end of the ramp is located at or adjacent the aperture, and a second unobstructed end is raised with respect to said obverse face and spaced from said cuff such that the ramp is capable of guiding, during use, an object travelling from the aperture along the ramp, beyond the mask.

14. A device as claimed in claim 12, wherein said ramp is curved.

15. A device as claimed in claim 1, wherein the mask comprises a body in which said aperture is formed and around which said cuff is located, and wherein said guide member includes a support portion, one end of which is connected to, or connectable to, said body, the support portion passing through the cuff.

16. A device as claimed in claim 15, wherein the free end of said support portion carries said inflatable balloon.

17. A device as claimed in claim 16, wherein the cuff, or at least part of it, is inflatable and wherein said cuff and said balloon are interconnected by a neck portion extending around said support portion.

18. A device as claimed in claim 1, further including a venting channel having a first end opening at the free end of said guide member and a second end opening beyond the mask with respect to said guide member.

19. A device as claimed in claim 18, wherein said venting channel comprises a tube and/or passageway extending through said guide member and at least partially along said airway tube.

20. A device as claimed in claim 1, wherein said inflatable balloon is shaped to be rounded when inflated.

21. A device as claimed in claim 20, wherein said inflatable balloon is positioned around said free end of said guide member to inflate substantially symmetrically around said free end.

22. An airway device comprising:
   an airway tube;
   a laryngeal mask, the mask being shaped to define an aperture, the aperture being in fluid communication with the airway tube;
   a peripheral cuff at least partly surrounding said aperture, the cuff having a tip for insertion, in use, into a patient's oesophagus;
   a guide member projecting from said tip of said peripheral cuff and having a free end spaced apart from said tip; and
   a blocking member, provided on said guide member, for blocking, in use, said patient's oesophagus, wherein said blocking member comprises an inflatable balloon that is shaped to be rounded when inflated and is positioned around said free end of said guide member to inflate substantially symmetrically around said free end.

* * * * *